United States Patent
Gruber et al.

(10) Patent No.: US 6,469,181 B1
(45) Date of Patent: Oct. 22, 2002

(54) PROCESS FOR PREPARING 2-OXINDOLES AND N-HYDROXY-2-OXINDOLES

(75) Inventors: John M. Gruber, Mountain View; A. Ray Bulls, Sunnyvale; John H. Grate, Mountain View, all of CA (US)

(73) Assignee: Catalytica, Inc., Mountain View, CA (US)

( * ) Notice: Subject to any disclaimer, the term of this patent is extended or adjusted under 35 U.S.C. 154(b) by 0 days.

(21) Appl. No.: 08/380,765

(22) Filed: Jan. 30, 1995

(51) Int. Cl.$^7$ ............................................. C07D 209/34

(52) U.S. Cl. ........................................ 548/486; 560/23

(58) Field of Search ............................ 548/486; 560/23

(56) References Cited

U.S. PATENT DOCUMENTS

| | | | |
|---|---|---|---|
| 3,634,453 A | 1/1972 | McManus et al. | 260/325 |
| 3,882,236 A | 5/1975 | Molloy | 424/274 |
| 4,160,032 A | 7/1979 | Hardtmann | 424/274 |
| 4,556,672 A | 12/1985 | Kadin | 514/414 |
| 4,569,942 A | 2/1986 | Kadin | 514/414 |
| 4,721,712 A | 1/1988 | Kadin | 514/253 |
| 5,210,212 A | 5/1993 | Dugger | 548/486 |
| 5,284,960 A | 2/1994 | Imwinkelried et al. | 548/486 |

FOREIGN PATENT DOCUMENTS

| | | | |
|---|---|---|---|
| GB | 1158532 | * | 7/1969 |
| WO | 93/09077 | * | 5/1993 |

OTHER PUBLICATIONS

March, J.; "Advanced Organic Chemistry", 3rd Ed., John Wiley & Sons, New York, @1985, pp. 792–793.*
Abramovitch et al., "Internuclear Cyclisation. Part VIII. Naphth.[3 : 2: 1–cd ]oxindoles,"*J. Amer. Chem. Soc.* month not available (1954) 3:1697–1703.
Atkinson et al., "Nucelophilic Displacement of Activated Aryl Triflates a New Synthesis of Oxindoles and Arylacetic Acids," *Tetrahedron Letters* No. 31 month not available (1979) pp. 2857–2860.
Beckett et al., "Substituted Oxindoles—1: The Preparation and Spectral Characteristics of Some Simple Oxindole Derivatives," *Tetrahedron* month not available (1968) 24:6093–6109.
Carson et al., "The Synthesis and Properties of 2–p–Dimethylaminophenyl–1,3,3–trimethyl–3H–indolium Salts," *J. Amer. Chem. Soc.* month not available (1965) pp. 5819–5825.
Di Carlo, "Synthesis of Oxindole," *J. Amer. Chem. Soc.* month not available (1944) 66: 1420.
Endler et al., "3–Methyloxindole," *Org. Synth.* month not available (1963) IV:657–659.
Entwistle et al., "Rapid Catalytic Transfer Reduction of Aromatic Nitro Compounds to Hydroxylamines," *Tetrahedron*, 34:213–215 month not available 1978.

Freifelder, *Practical Catalytic Hydrogenation*, Wiley–Interscience, NY month not available (1971) pp. 168–206.
Gassman et al., "Oxindoles. A New, General Method of Synthesis," *J. Amer. Chem. Soc.* Aug. (1974) 96:17, pp.5508–5512.
Giovannini et al., *Helv. Chim. Act* month not available (1948) 31:1392–1396.
Jackson et al., "On Tetrabromdinitrolbenzol," *Amer. Chem. J.*, May (1890) 12:295–306.
Johnstone et al., "Heterogeneous Catalytic Transfer Hydrogenation and Its Relation to Other Methods for Reduction of Organic Compounds," *Chem. Rev.*, month not available (1985) 85:129–170.
Koelsch, "A Synthesis of Ethyl Qunininate from *m*–Cresol," *J. Amer. Chem. Soc.* Dec. (1944) 66:2019–2020.
Mudryk, *Synthesis* Dec. (1988) pp. 1007–1009.
Quallich et al., "A General Oxindole Synthesis," *Synthesis* Jan. (1993) pp. 51–53.
RajanBabu et al., " –Nitroacrylation of Ketones and Esters: An Exceptionally Facile Synthesis of Indoles, 2–Indolinones, and Arylacetic Acids," *J. Org. Chem.* month not available (1986) 51:1704–1712.
Rylander, "Hydrogenation of Nitro Compounds," *Catalytic Hydrogenation in Organic Synthesis*, Academic Press, NY no month available (1979) pp–113–137.
Simet, "The Preparation of 6–Triffluoromethylisatin," *J. Org. Chem.* month not available (1963) 28:3580–3581.
Sumpter, "The Chemistry of Oxindole," *Chem. Rev.* month not available (1945) 37:443479.
Sundberg, *The Chemistry of Indoles* month not available (1970) Academic Press, NY, pp. 341–393.

(List continued on next page.)

*Primary Examiner*—Laura L. Stockton
(74) *Attorney, Agent, or Firm*—Townsend and Townsend and Crew LLP

(57) ABSTRACT

The present invention provides a processes, having practical utility, for preparing 2-oxindoles, N-hydroxy-2-oxindoles, or mixtures thereof comprising: catalytically hydrogenating a 2-nitroarylmalonate diester to produce a 2-(N-hydroxyamino)arylmalonate diester, a 2-aminoarylmalonate diester, or mixtures thereof as a first reaction intermediate; cyclizing, by intramolecular aminolysis of one ester group, the first reaction intermediate to produce a N-hydroxy-2-oxindole-3-carboxylate ester, 2-oxindole-3-carboxylate ester, or mixtures thereof as a second reaction intermediate; and hydrolyzing and decarboxylating the remaining ester group of the second reaction intermediate to produce the N-hydroxy-2-oxindole, the 2-oxindole, or mixtures thereof, wherein the cyclization reaction and the hydrolysis and decarboxylation reaction are conducted in situ with the catalytic hydrogenation reaction without isolation of said reaction intermediates.

19 Claims, No Drawings

OTHER PUBLICATIONS

Walker, "Synthesis of 5, 6–Dimethoxyindoles and 5,6–Dimethoxyoxindoles. A New Systhesis of Indoles," *J. Amer. Chem. Soc.* Jul. (1955) 77:3844–3850.

Walsh et al., "Antiinflammatory Agents. Synthesis and Pharmacological Evaluation of 2–Amino–3–benzoylphenyl-acetic Acid and Analogues," *Amer. Chem. Soc.* Nov. (1984) 27:11:1379–1388.

Wright et al. "Cyclic Hydroxamic Acids Derived from Indole," *J. Amer. Chem. Soc.* Jan. (1956) 78:221–224.

Zhang et al. "Effects of Electron Acceptors and Radical Scavengers on Nonchain Radical Nucleophilic Substitution Reactions," *J. Org. Chem.* month not available (1993) 58:224–227.

* cited by examiner

PROCESS FOR PREPARING 2-OXINDOLES AND N-HYDROXY-2-OXINDOLES

FIELD OF THE INVENTION

This invention relates generally to preparing 2-oxindoles and N-hyroxy-2-oxindoles. 2-oxindoles are also known as 2-oxoindolines and as indole-2(3H)-ones, and oxindole(s) as used herein, refers to 2-oxindole(s). More specifically, this invention relates to preparing 2-oxindoles and N-hyroxy-2-oxindoles via reduction of 2-nitroarylmalonate diesters. It further relates to preparing 2-nitroarylmalonate diesters from 2-halonitroarenes, for subsequent reduction to prepare 2-oxindoles or a N-hyroxy-2-oxindoles.

2-oxindoles are valuable pharmaceutical agents and/or intermediates for the production of pharmaceutical agents, including analgesic and anti-inflammatory agents (U.S. Pat. No. 4,721,712), anti-anxiolytic agents (U.S. Pat. No. 3,882,236), and sleep-inducing agents (U.S. Pat. No. 4,160,032). N-hyroxy-2-oxindoles are useful intermediates in the preparation of certain 5-substituted-2-oxindoles (U.S. Pat. No. 5,210,212).

BACKGROUND OF THE INVENTION

Sundberg, *The Chemistry of the Indoles*; Academic, New York, 1970, p. 341 and Sumpter, *Chem. Rev., vol.* 37 (1945), 443 give overviews of the synthesis and chemistry of oxindoles. U.S. Pat. Nos. 3,634,453; 4,556,672; and 4,569,942 describe preparations of 2-oxindoles. Oxindoles can be prepared by the reduction of isatins, for example by Wolff-Kishner reduction using first hydrazine hydrate, then sodium alcoholate in alcohol. (See Examples in U.S. Pat. No. 4,721,712.) This method has the drawback of using hydrazine, and for substituted oxindoles, is limited by the availability 30 and difficulty of producing appropriately substituted isatins.

Quallich et al., *Synthesis, vol.* 1993 (1993), p. 51 summarizes methods for preparing oxindoles. Noting that a general synthetic method for preparing oxindoles which controls the regiochemistry about the aromatic ring was desired, Quallich et al. state, (inserting footnoted references in brackets): "Many oxindole synthesis in the literature have not controlled the aromatic substitution pattern because they were based on intramolecular bond connections of aniline derivatives which did not effectively discriminate between the two available ortho positions. [The Sundberg and Sumpter references are cited.] These include the Friedel-Crafts alkylations of α-chloro acetanilides [Abramovitch et al. *J. Chem. Soc., vol.* 1954, p. 1697], Gassman cyclization of azasulfonium salts [Gassman et al., *J. Am. Chem. Soc., vol* 96 (1974), p. 5508], and thermally induced cyclization of N-acyl phenylhydrazides [Carlson et al., *J. Chem. Soc., vol.* 1965, p. 5419; Endler et al., *Org Synth. Vol. IV* (1963), 657]. Ring closure to the oxindole by the aforementioned methods often afforded a mixture of products unless the starting material was symmetrical (para-substituted). In addition, other limitations are imposed on the ring substituents due to the harsh conditions of the preceding methods. Vicarious nucleophilic substitution [Mudryk et al., *Synthesis, vol.* 1988, p. 1007] and addition of ketene silyl acetals [Rajanbabu et al., *J. Org. Chem., vol.* 51 (1986), p. 1704] to nitrobenzenes has also been employed to prepare oxindoles, but these methods do not always provide regiocontrol. One method which had given control over oxindole regiochemistry was the funtionalization of nitrotoluenes [Beckett et al., *Tetrahedron, vol* 1968, 6093], but the lack of commercial availability of these compounds was a limitation. Substitution of a triflate [Atkinson et al., *Tetrahedron Lett., vol* 1979, 2857] or bromide [Walsh et al., *J. Med. Chem., vol* 27 (1984), p. 1379] in a nitrobenzene by malonate and subsequent conversion into an oxindole was precedented although the generality of these routes was not known."

Quallich et al. discloses a three-step process to produce oxindoles from 2-halonitrobenzenes. In the first step, a 2-halonitrobenzene is reacted with a malonate diester anion (generated from the malonate diester by sodium hydride) to produce, after acidification, a 2-nitrophenylmalonate diester, which was isolated. In the second step, the 2-nitrophenylmalonate diester was treated with one equivalent of water and two equivalents of lithium chloride in dimethylsulfoxide to effect the Krapcho hydrolysis and decarboxylation of one of the ester groups, affording the 2-nitrophenylacetate ester, which was isolated. In the third step, the nitro group of the 2-nitrophenylacetate ester was reduced with a four mole ratio of elemental iron powder in acetic acid at 100° C. to yield, after isolation, the oxindole. This process has the drawback of multiple process steps, with intermediate isolations of process intermediates as purified solids and cumulative low yields. For example, the overall mole yields of 5-chloro-2-oxindole, 6-chloro-2-oxindole, and 6-methoxy-2-oxindole from the corresponding substituted 2-chlorobenzenes, calculated from the reported yields of the individual steps, is 31%, 49%, and 16%, respectively. This also has the drawback of generating substantial waste streams, including multiple stoichiometric quantities of iron wastes.

Quallich et al. further disclose that the 2-nitrophenylmalonate diesters are formed in good yield in the first step except where an electron-donating substituent is present. This is exemplified by only 33% yield of 4-methoxy-2-nitrophenylmalonate diester from 2-chloro-5-methoxynitrobenzene, containing the electron-donating methoxy group para to the chloride being substituted, compared to 80% yield for the 6-chloro-2-nitrophenylmalonate diester from the corresponding 2,5-dichloronitrobenzenes, containing chloride in that para position, and further compared to their 76% and 85% yields for 4-bromo- and 4-fluoro-2-nitrophenylmalonate diesters from the corresponding 2,5-dibromo- and 2,5-difluoro- halonitrobenzenes, respectively.

Simet, *J. Org. Chem, vol.* 28 (1963), p. 3580 reports a similar process for preparing 6-trifluoromethyl-2-oxindole from 5-trifluoromethyl-2-chloronitrobenzene, by reaction with a malonate diester anion, followed by caustic hydrolysis and decarboxylation to obtain the 4-trifluromethyl-2-nitrophenylacetic acid. After isolation, this was reduced to the 6-trifluoromethyl-2-oxindole with about a 5 mole ratio of mossy tin metal in 9 N hydrochloric acid (called the Baeyer method). This process likewise has the drawback of multiple process steps, and the severe drawback of generating substantial waste streams, including multiple stoichiometric quantities of tin wastes.

Giovannini et al., *Helv., vol.* 31 (1948), p. 1392, reports a related multistep process for preparing 6-carboxy-2-oxindole from 4-cyano-2-bromo-nitrobenzene, using iron (II)sulfate in ammoniacal water to reduce the nitro group in the substituted 2-nitrophenylacetic acid to produce the 2-oxindole.

There are other reports of the conversion substituted 2-nitrophenylacetic acids or esters (which are derived by methods other than via the 2-nitrophenylmalonate diester) to substituted 2-oxindoles, and sometimes N-hydroxy-2- oxindoles, by reduction with active metals, typically iron metal, tin metal, or zinc metal, and acid. (See the Sumpter reference; Simet, *J. Org. Chem, vol.* 28 (1963), p. 3580; Wright et al, *J. Am. Chem. Soc., vol* 78 (1956), p. 221.) These processes have the common drawback of using excess active metal reductants in acids with the resulting generation of large amounts of spent metal wastes.

A couple reports disclose converting 2-nitrophenylmalonate diesters to oxindoles, without prior hydrolysis and decarboxylation to the 2-nitrophenylacetate ester or free acid, by using such stoichiometric active metal reductants. Jackson et al., *Am. Chem. J., vol. XII* (1890), p. 23 reduces a dibromodinitrophenylmalonate diester with tin and concentrated hydrochloric acid in methanol to obtain a bromoamido-oxindole. Similarly, Walsh et al. (cited above in the quote from Quallich et al.) reduces 4-benzoyl-2-nitrophenylmalonate diester with tin, at greater than 3 mole equivalents, and concentrated hydrochloric acid in ethanol to obtain 6-benzoyl-2-oxindole. These processes have the drawbacks of intermediate isolations of the 2-nitrophenylmalonate diesters as purified solids, and the generation of substantial waste streams, including multiple stoichiometric quantities of tin wastes. Even though aware of Walsh et al., Quallich et al. chose to separately hydrolyze and decarboxylate their 2-nitrophenylmalonate diesters to 2-nitrophenylacetate ester in their second step prior to reducing the nitro group in their third step.

There are a several reports of reduction of 2-nitrophenylacetic acids or esters to 2-oxindoles via catalytic hydrogenation, including Di Carlo, *J. Am. Chem. Soc., vol.* 66 (1944), p. 1420; Koelsch, *J. Am. Chem. Soc., vol.* 66 (1944), p. 2019; Walker, *J. Am. Chem. Soc., vol.* 77 (1955), p. 3844; Beckett et al., *Tetrahedron, vol.* 24 (1968), p. 6093; U.S. Pat. No. 4,160,032; U.S. Pat. No. 5,284,960, and the Atkinson et al. and Rajanbabu et al. references cited above in the quote from Quallich et al. Atkinson et al. shows a 2-nitroarylmalonate diester, which is hydrolyzed and decarboxylated with hydrochloric and acetic acid to the 2-nitroarylacetic acid, which is then hydrogenated to obtain the 2-oxindole. The other listed references obtain their 2-nitrophenylacetic acids or esters by different multistep methods not involving 2-nitroarylmalonate diesters.)

U.S. Pat. No. 5,284,960 reports a three step process for the production of 5-chloroxindole via 4-chloro-2-nitrophenyl acetate ester, starting from 4-chloronitrobenzene and combining stepwise three previously known reactions: 1) The 4-chloronitrobenzene is reacted with chloroacetate ester in the presence of a base to form 4-chloro-2-nitrophenylacetate ester. This very reaction on this specific substrate to give this specific product was previously reported by the Mudryk et al. reference cited above in the quote from Quallich et al. Mudryk et al. specifically comments that the 2-nitroarylacetate esters are precursors to oxindoles, citing the Walker and Simet references mentioned above. 2) The 4-chloro-2-nitrophenyl acetate ester is catalytically hydrogenated to the corresponding 4-chloro-2-aminophenyl acetate ester. Catalytic hydrogenations of chloronitroaromatics to chloroanilines are well-known industrially practiced reactions. 3) The 4-chloro-2-aminophenyl acetate ester is cyclized to 5-chlorooxindole in the presence of acid. This is an acid-catalyzed intramolecular anilinolysis of the ester group. (Steps 2 and 3 accomplish what Rajanbabu et al., discussed above, reported to be accomplished in one step: catalytic hydrogenation of 4-chloro-2-nitrophenyl acetate ester with in situ cyclization to 5-chlorooxindole.) The exemplified process in U.S. Pat. No. 5,284,960 has the drawbacks of multiple process steps, conducting the first reaction cryogenically in liquid ammonia and using metallic sodium, and isolation of the 4-chloro-2-nitrophenyl acetate ester intermediate as a dry solid.

U.S. Pat. No. 5,210,212 discloses that N-hydroxy-6-chloro-2-oxindole can be obtained by the reaction of 4-chloro-2-(N-hydroxyamino)phenylacetate methyl ester with aqueous 50% sulfuric acid in ethanol. The 2-(N-hydroxyamino)phenylacetate was prepared from 4-chloro-2-nitrophenylacetate methyl ester by reduction with sodium hypophosphite using palladium on carbon catalyst, for which Johnstone et al., *Tetrahedron, vol.* 34 (1978), p. 213 is referenced. This method has the drawbacks of multiple process steps, with intermediate isolations of solids, including the undisclosed preparation and isolation of the 4-chloro-2-nitrophenylacetate methyl ester.

Zhang et al., *J. Org. Chem., vol.* 58 (1993), p. 224 discloses mechanistic studies of the nucleophilic substitution reaction ethyl cyanoacetate anion with 2-chloronitrobenzene and 2-bromonitrobenzene to form 2-nitrophenyl-α-cyano-acetate ethyl ester and concludes the results are consistent with a non-chain radical nucleophilic substitution mechanism.

OBJECTS OF THE INVENTION

The object of this invention is to provide an economically and environmentally preferable, effective and efficient process for the preparation 2-oxindoles and/or N-hydroxy-2-oxindoles. Further objects of this invention are to provide such processes having one or more of the following characteristics: 1) General for preparing a variety of substituted 2-oxindoles and/or N-hydroxy-2-oxindoles. 2) Starts from commonly available raw materials, like 2-halonitroarenes. 3) Provides controlled regiochemistry about the aromatic ring to produce the desired oxindole product, avoiding wasteful isomeric oxindole co-products, and the additional economic and environmental costs of separating and disposing them. 4) Avoids the use of active metal reductants and their attendant generation of excessive spent metal wastes. 5) Avoids the use of hazardous reagents typical of background oxindole processes. 6) Minimizes the number of process reaction steps, particularly avoiding the separate step of hydrolyzing and decarboxylating a 2-nitrophenymalonate diester to a 2-nitrophenyacetatic acid or ester prior to catalytic hydrogenation to a 2-oxindole or N-hydroxy-2-oxindole. 7) Minimizes the number of other process operations, including avoiding any need to isolate process intermediates as purified solids, with attendant yield losses and economic costs and concomitant filtrate wastes and disposal costs. 8) Readily scaleable for production of commercial-scale quantities (10's to 10,000's of Kgs) of 2-oxindoles and/or N-hydroxy-2-oxindoles or derivatives thereof.

Another object of this invention is to provide an effective and efficient process for the preparation of substituted 2-nitrophenylmalonate diesters from substituted 2-halonitrobenzenes even when an electron-donating substituent is present. A further object of this invention to provide a process with higher overall yield of substituted 2-nitrophenylmalonate diesters from substituted 2-halonitrobenzenes containing an electron-donating substituent than are obtained in the background references from the reaction of 2-halonitrobenzenes with a malonate diester anion.

The present invention is directed towards one or more of the above objects. Other objects and advantages will become apparent to persons skilled in the art and familiar with the background references from a careful reading of this specification.

SUMMARY OF INVENTION

Applicants unexpectedly and surprisingly discovered that upon catalytically hydrogenating the nitro group of a 2-nitroarylmalonate diester, the initially produced 2-aminoarylmalonate diester and/or 2-(N-hydroxyamino) arylmalonate diester readily cyclizes in situ by intramolecular aminolysis of one ester group to produce a 2-oxindole-3-carboxylate ester and/or a N-hyroxy-2-oxindole-3-carboxylate ester, respectively, and further unexpectedly and surprisingly discovered that the 3-carboxylate ester group (the remaining ester group) in these species can be readily hydrolyzed and decarboxylated in situ to produce the 2-oxindole and/or the N-hyroxy-2-oxindole. Applicants surprising found that the ester hydrolysis and decarboxylation in these 3-carboxylate ester intermediates is unexpectedly facile and will occur readily even when no water is introduced to the reaction mixture, so that the only water present is the one to two mole equivalents of water created by reduction of the nitro group to the N-hydroxyamino or amino group, respectively, and even in the absence of any acid such as is usually used to effect the hydrolysis and decarboxylation of ester groups. This surprising discovery provided the inventive process having the advantage of eliminating the need, taught by the background references, to first hydrolyze and decarboxylate the 2-nitroarylmalonate diester to obtain the 2-nitroarylacetic acid or ester in a separate process step prior to the catalytic hydrogenation reaction step.

Applicants found that process reaction conditions could be adjusted to obtain either the 2-oxindole or the N-hydroxy-2-oxindole as the predominant product after completion of the in situ cyclization and in situ hydrolysis and decarboxylation, and that either the 2-oxindole of the N-hydroxy-2-oxindole could be so-produced as the isolated product. Applicants further found that, in a process to produce a 2-oxindole, when the N-hydroxy-2-oxindole remained as major or minor product after completion of the in situ cyclization and in situ ester hydrolysis and decarboxylation, it can be further catalytically hydrogenated in situ to produce the 2-oxindole in high selectivity and yield.

Accordingly, the present invention provides a processes, having practical utility, for preparing 2-oxindoles, N-hydroxy-2-oxindoles, or mixtures thereof comprising: catalytically hydrogenating a 2-nitroarylmalonate diester to produce a 2-(N-hydroxyamino)arylmalonate diester, a 2-aminoarylmalonate diester, or mixtures thereof as a first reaction intermediate; cyclizing, by intramolecular aminolysis of one ester group, the first reaction intermediate to produce a N-hydroxy-2-oxindole-3-carboxylate ester, 2-oxindole-3-carboxylate ester, or mixtures thereof as a second reaction intermediate; and hydrolyzing and decarboxylating the remaining ester group of the second reaction intermediate to produce the N-hydroxy-2-oxindole, the 2-oxindole, or mixtures thereof, wherein the cyclization reaction and the hydrolysis and decarboxylation reaction are conducted in situ with the catalytic hydrogenation reaction without isolation of said reaction intermediates. The present invention further provides a process comprising the just recited process and further comprising catalytically hydrogenating the N-hydroxy-2-oxindole to produce the 2-oxindole, wherein this further catalytic hydrogenation reaction is conducted in situ with the preceding catalytic hydrogenation, cyclization, and hydrolysis and decarboxylation reactions without isolation of the N-hydroxy-2-oxindole.

While not intending to be bound by theory, Applicants believe that the unexpected facility with which 2-aminoarylmalonate diesters and 2-(N-hydroxyamino) arylmalonate diester cyclize by intramolecular aminolysis of one ester group is made possible by the presence of the other ester group. There are several speculative ways the presence of two ester groups might promote the cyclization: 1) By simply doubling the number of ester groups for the 2-amino or 2-(N-hydroxyamino) group to react with; 2) By sterically forcing at least one ester group to be more frequently rotated into position for intramolecular attack by the 2-amino or 2-(N-hydroxyamino) group; 3) By intramolecular hydrogen bonding in the tautomeric structure illustrated by (I) below, polarizing the remaining carbonyl in the tautomer to intramolecular attack by the 2-amino or 2-(N-hydroxyamino) group; and 4) By stabilizing the developing negative charge in the tetrahedral intermediate by bringing it into conjugation with the π-system including the aromatic ring, as illustrated in the tautomeric structure (II) below. A possible mechanism incorporating possibilities 3) and 4) is illustrated for the case of a 2-(N-hydroxyamino) phenylmalonate diester as follows (wherein R is an alkyl group as defined for $R^1$ and $R^2$ herein below):

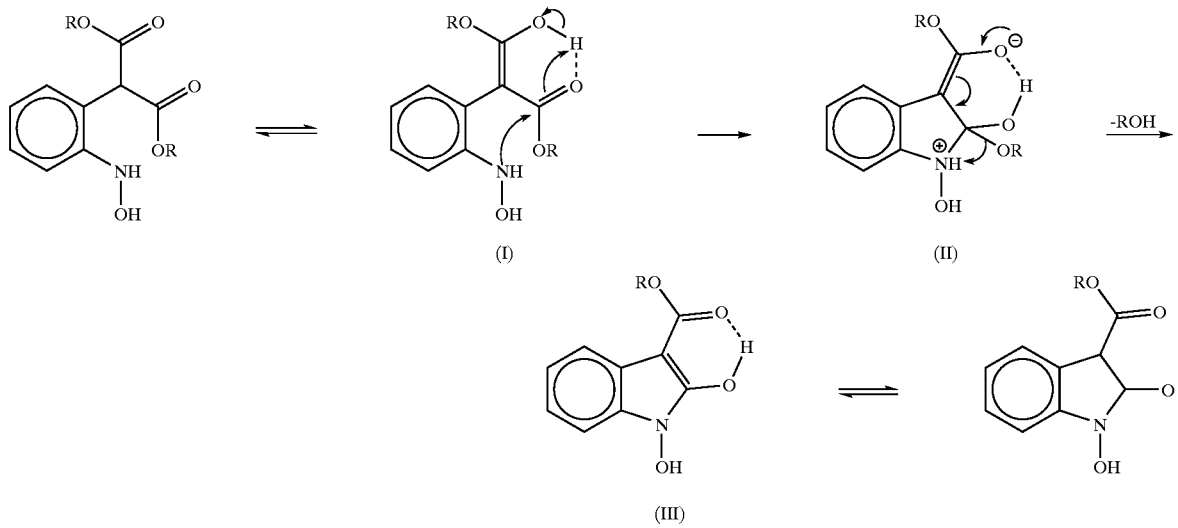

In essence, possibility 3) means that the tautomeric form of the second ester group functions intramolecularly like an acid catalyst, and possibility 4) makes it a stronger acid for that function.

While not intending to be bound by theory, Applicants further believe that the surprising facility with which the 2-oxindole-3-carboxylate esters and N-hyroxy-2-oxindole-3-carboxylate esters are hydrolyzed and decarboxylated, even in the absence of an added acid catalyst, is similarly due to such intramolecular hydrogen bonding and acidity and in the tautomeric structure illustrated by (III) above and below, polarizing the remaining ester carbonyl to attack by water, and by stabilization of the developing negative charge in the tetrahedral intermediate by moving it into conjugation with the π-system including the aromatic ring, as illustrated by the intermediate structure (IV) below. A speculative mechanism incorporating these possibilities is illustrated for the case of a N-hyroxy-2-oxindole-3-carboxylate ester as follows (wherein R is an alkyl group as defined for $R^1$ and $R^2$ herein below):

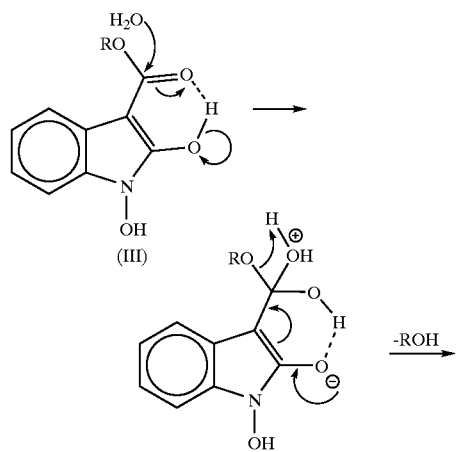

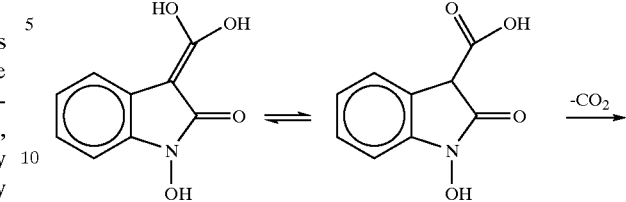

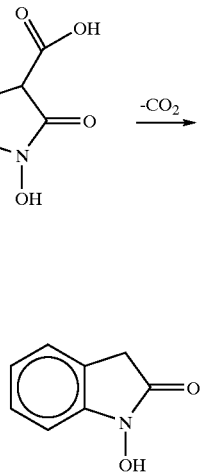

Applicant's investigation of the overall conversion of 2-nitroarylmalonate diesters into 2-oxindoles, N-hydroxy-2-oxindoles, or mixtures thereof by the inventive process of catalytic hydrogenation with in situ cylization by intramolecular ester arninolysis and in situ ester hydrolysis and decarboxylation revealed that these reactions occur in this stated order. Facile ester hydrolysis and decarboxylation occurs after cyclization to form the 2-oxindole-3-carboxylate ester structure, and does not readily occur in the preceding uncyclized intermediates. This is illustrated below showing the dominant reaction pathways for the conversion of a 2-nitrophenylmalonate diester to 2-oxindole or N-hydroxy-2-oxindole.

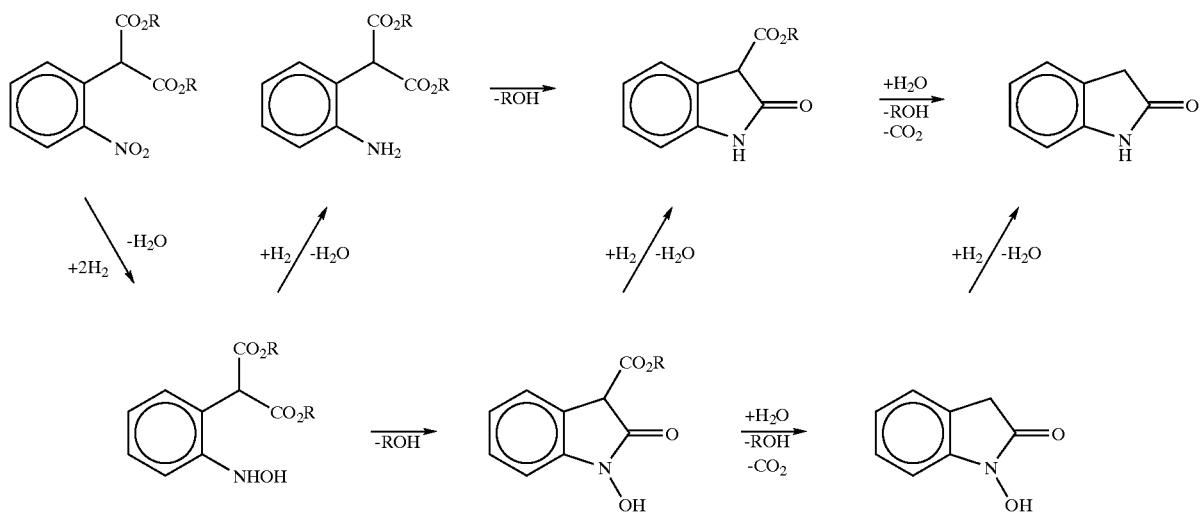

The 2-nitrophenylmalonate diester is first hydrogenated to a 2-(N-hydroxyamino)phenylmalonate diester or further hydrogenated to a 2-aminophenylmalonate diester as the first intermediates in the overall conversion. The 2-(N-hydroxyamino)phenylmalonate diester and 2-aminophenylmalonate diester each undergo cyclization by intramolecular aminolysis of one of the ester groups by the 2-(N-hydroxyamino) and 2-amino group, respectively, to form the N-hydroxy-2-oxindole-3-carboxylate ester and the 2-oxindole-3-carboxylate ester, respectively, as second reaction intermediates. Subsequent facile hydrolysis and decarboxylation of these intermediates forms the N-hyroxy-2-oxindole and the 2-oxindole, respectively.

The N-hydroxy-2-oxindole-3-carboxylate ester intermediate can be further catalytically hydrogenated in situ to the 2-oxindole-3-carboxylate ester and the N-hyroxy-2-oxindole can be further catalytically hydrogenated in situ to the 2-oxindole during the course of the process. When the 2-oxindole is the desired product and N-hyroxy-2-oxindole is also formed in the process, catalytic hydrogenation is typically continued, often under more forcing conditions, to convert the N-hyroxy-2-oxindole to the 2-oxindole in situ.

The present invention further provides processes for preparing a 2-oxindole, a N-hydroxy-2-oxindole, or mixtures thereof comprising reacting a 2-halonitroarene with a malonate diester anion and then acidifying to produce a 2-nitroarylmalonate diester; and converting the 2-nitroarylmalonate diester to the 2-oxindole, N-hydroxy-2-oxindole, or mixtures thereof by the inventive process of catalytic hydrogenation with in situ cyclization and in situ hydrolysis and decarboxylation, described above.

Applicants also unexpectedly and surprisingly discovered that substituted 2-halonitrobenzenes comprising an electron-donating substituent that do not afford 2-nitrophenylmalonate diesters in good yield on reaction with malonate diester anions, react with cyanoacetate ester anions to afford 2-nitroaryl-α-cyanoacetate esters in good yield, and that subsequent alcoholysis of the cyano group of these 2-nitroaryl-α-cyanoacetate esters provides the desired 2-nitrophenylmalonate diesters in overall good yield.

Accordingly, the present invention additionally provides a process for preparing a 2-nitroarylmalonate diester, comprising reacting a 2-halonitroarene with a cyanoacetate ester anion and then acidifying to produce a 2-nitroaryl-α-cyanoacetate ester; and alcoholyzing the 2-nitroaryl-α-cyanoacetate ester to produce the 2-nitroarylmalonate diester.

Consequently, the present invention further provides a process for preparing a 2-oxindole, N-hydroxy-2-oxindole, or mixtures thereof comprising: reacting a 2-halonitroarene with a cyanoacetate ester anion and then acidifying to produce a 2-nitroaryl-α-cyanoacetate ester; alcoholyzing the 2-nitroaryl-α-cyanoacetate ester to produce a 2-nitroarylmalonate diester; and converting the 2-nitroarylmalonate diester to the 2-oxindole, N-hydroxy-2-oxindole, or mixtures thereof by the inventive process of catalytic hydrogenation with in situ cyclization and in situ hydrolysis and decarboxylation, described above.

While not intending to be bound by theory, Applicants speculate that the reactions of 2-halonitroarenes with cyanoacetate ester anions proceed by an electronic mechanism that is different than that of their reactions with malonate diester anions, and that mechanism does not build up as much negative charge on aromatic ring carbons in the rate-limiting transition state and so is not as disfavored by electron donating substituents. Perhaps the substitution of halide by the malonate diester anion occurs by the $S_N2Ar$ nucleophilic addition-elimination substitution mechanism, with nucleophilic addition of the anion to the halide-bearing carbon, generating an intermediate with a full negative charge in the aromatic ring. Perhaps the substitution of halide by the cyanoacetate ester anion occurs by a nonchain radical nucleophilic substitution mechanism, with only a single electron transfer to the aromatic structure, generating a radical anion, during the rate limiting step.

In certain processes of the present invention, the 2-nitroarylmalonate diester produced from the 2-halonitroarene may be converted to the 2-oxindole or N-hydroxy-2-oxindole without its isolation as a purified solid. In certain other processes of the present invention, the 2-nitroaryl-α-cyanoacetate ester produced from the 2-halonitroarene may be converted to the 2-nitroarylmalonate diester without its isolation in solid form. The present invention provides efficient processes for the conversion of 2-halonitroarenes to 2-oxindoles and N-hydroxy-2-oxindoles having no isolations of solid intermediates in purified forms.

DETAILED DESCRIPTION OF THE INVENTION

Suitable starting materials and intermediates for conversion into 2-oxindoles and N-hyroxy-2-oxindoles by the process of the present invention include 2-halonitroarenes in general, 2-nitroaryl-α-cyanoacetate esters in general, and 2-nitroarylmalonate diesters in general. Particularly suitable 2-halonitroarenes, 2-nitroaryl-α-cyanoacetate esters, 2-nitroarylmalonate diesters include those having the structural formulas (V), (VI), and (VII), respectively:

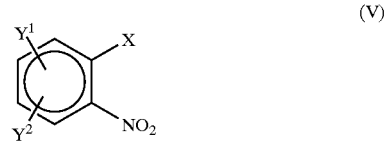

(V)

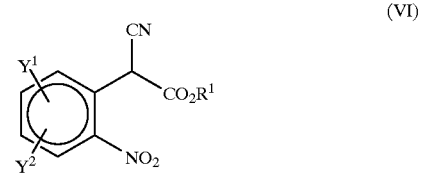

(VI)

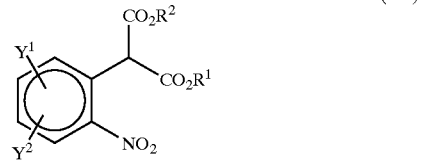

(VII)

wherein
X is a halo group selected from the group consisting of fluoro, chloro, bromo, and iodo, preferably selected from the group fluoro, chloro, or bromo;
$Y^1$ and $Y^2$ are each independently selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, phenyl, alkanoyl having 2 to 4 carbons, benzoyl, thenoyl, alkanamido having 2 to 4 carbons, benzamido N,N-dialkylsulfamoyl having 1 to 3 carbons in each of said alkyls, nitro, N-hydroxyamino, amino, alkylamino having 1 to 4 carbons, dialkylamino having 1 to 4 carbons in each of said alkyls, and benzylamino;

or $Y^1$ and Y2 when taken together are a 4,5-, 5,6- or 6,7-methylenedioxy group or a 4,5-, 5,6- or 6,7-ethylenedioxy group;

or $Y^1$ and $Y^2$ when taken together and when attached to adjacent carbon atoms, form a divalent radical Z, wherein Z is selected from the group consisting of

$Z^1$

$Z^2$

$Z^3$

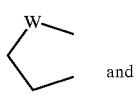
$Z^4$
and

$Z^5$ wherein W is oxygen or sulfur;

$R^1$ and $R^2$ are each independently selected from the group consisting of methyl, ethyl, n-propyl, i-propyl, n-butyl, i-butyl, and t-butyl.

Typically, $R^1$ and $R^2$ are each independently selected from the group consisting of methyl and ethyl. Preferably, $R^1$ and $R^2$ are the same and are selected from the group consisting of methyl and ethyl. Most preferably, $R^1$ and $R^2$ are methyl.

Electron donating substituent has the usual meaning in the art, and as used herein specifically refers to an electron donating substituent positioned ortho or para to the 2-halo group in the 2-halonitroarene.

Suitable N-hydroxy-2-oxindoles and 2-oxindole products are those that can be prepared by the process of present invention from 2-halonitroarenes in general, 2-nitroaryl-α-cyanoacetate esters in general, and 2-nitroarylmalonate diesters in general. Particularly suitable N-hydroxy-2-oxindoles, and 2-oxindoles include those having the structural formulas (VIII) and (IX), respectively:

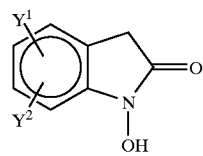
(VIII)

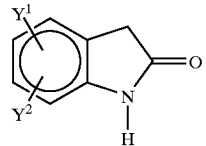
(IX)

wherein $Y^1$ and $Y^2$ are defined as above for structural formulas (V), (VI), and (VII), with the exception that nitro is not in the group from which $Y^1$ and $Y^2$ are selected. When the 2-halonitroarene, 2-nitroaryl-α-cyanoacetate ester, or 2-nitroarylmalonate diester has a nitro substituent, it is hydrogenated in the process of the invention to an amino or N'-hydroxyamino substituent in the resulting N-hydroxy-2-oxindole or 2-oxindole.

Reaction intermediates in the inventive conversion of 2-nitroarylmalonate diesters to N-hydroxy-2-oxindoles and 2-oxindoles are corresponding 2-(N-hydroxyamino) arylmalonate diesters, a 2-aminoarylmalonate diesters, N-hydroxy-2-oxindole-3-carboxylate esters, and 2-oxindole-3-carboxylate esters. Particularly suitable 2-(N-hydroxyamino)arylmalonate diesters, a 2-aminoarylmalonate diesters, N-hydroxy-2-oxindole-3-carboxylate esters, and 2-oxindole-3-carboxylate esters include those having the structural formulas (X), (XI), (XII), and (XIII), respectively:

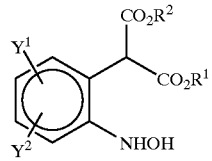
(X)

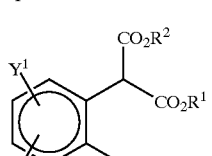
(XI)

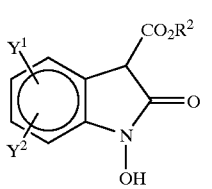
(XII)

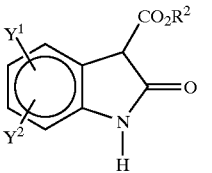
(XIII)

wherein $Y^1$ and $Y^2$ are defined as above for structural formulas (VIII) and (IX), and $R^1$ and $R^2$ are defined as above for structural formulas (V), (VI), and (VII).

Suitable cyanoacetate ester and malonate diester starting materials for the process of the present invention are, respectively, cyanoacetate esters in general and malonate diesters in general, and have the general structural formulas (X) and (XI), respectively:

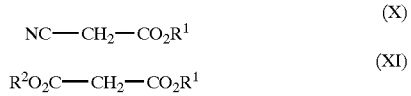

$$NC-CH_2-CO_2R^1 \quad (X)$$

$$R^2O_2C-CH_2-CO_2R^1 \quad (XI)$$

wherein $R^1$ and $R^2$ are hydrocarbyl groups and particularly suitable $R^1$ and $R^2$ are defined as above for structural formulas (VI) and (VII).

The cyanoacetate ester anion or malonate diester anion is generated in solution from the cyanoacetate ester or malonate diester, respectively, before its reaction with the 2-halonitroarene. The generation of these anions in solution by reactions of the cyanoacetate ester or malonate diester with a suitable base that monodeprotonates the methylene ($CH_2$) group is well known in the art, and the methods known in the art can be used. Typically, the cyanoacetate ester or malonate diester is reacted with about an equimolar amount of the suitable base in a reaction inert solvent system comprising an aprotic polar solvent.

By reaction-inert solvent is meant a solvent system which does not react with the reactants or products of the reaction. The term solvent system is used to indicate that a single solvent or a mixture of two or more solvents can be used. Aprotic polar solvents are used to solubilize, at least in part, the base salt reactant and the cyanoacetate ester anion salt or malonate diester anion salt product, but the solvent system need not bring about complete solution of the reactants or products. Elevated temperature may be used to improve such solubility. Suitable aprotic polar solvents are well known in the art for various processes that involve producing in solution and subsequently reacting in solution such cyanoacetate ester anions or malonate diester anions. Preferred aprotic polar solvents included dimethylformamide, dimethylacetamide, N-methylpyrollidone, dimethylsulfoxide, and sulfolane.

Suitable bases are well known in the art and include alkali metal hydrides, releasing dihydrogen on reaction with the cyanoacetate ester or malonate diester, alkali metal amides, releasing amines on reaction with the cyanoacetate ester or malonate diester, and alkali metal alkoxides, forming the corresponding alcohol on reaction with the cyanoacetate ester or malonate diester. Preferred alkali metal countercations for the base, and consequently, for the cyanoacetate ester anion or the malonate diester anion, are lithium, sodium, and potassium for the base, and consequently, for the cyanoacetate ester anion or the malonate diester anion. Suitable alkali metal amides include sodamide, lithium diisopropylamide, and the like.

Typically, the cyanoacetate ester or malonate diester is used in at least an equimolar amount to the base, and preferably in a small molar excess, usually 1 to 25% molar excess, to ensure that essentially all the base is reacted to form the cyanoacetate ester anion or malonate diester anion, and none of the base remains to potentially react directly with the 2-halonitroarene.

Preferred bases, for practical economic and safe handling purposes, are alkali metal alkoxides, $RO^-M^+$, wherein R is defined as for $R^1$ and $R^2$, above, and M is an alkali metal, typically lithium, sodium, or potassium, and preferably sodium. Particularly preferred is sodium methoxide. Since alkoxide anions are not sufficiently basic to essentially completely deprotonate all the cyanoacetate ester or malonate diester at equilibrium when provided in about equimolar amounts, and since alkoxide anion can react directly with 2-halonitroarenes by nucleophilic substitution of alkoxide for halide, when alkoxide bases are used, the resulting alcohol is removed from the solution by distillation to pull the equilibrium acid-base reaction essentially to completion, leaving essentially no alkoxide or alcohol in solution and producing the cyanoacetate ester anion or malonate diester anion in equimolar amount to the initially added alkoxide. It will be understood that these anions have countercations in solution; for example, in the preferred embodiment using an alkali metal alkoxide as base, after distillation to pull the acid-base equilibrium and remove the provided alkoxide anion as the alcohol, the resulting solution comprises the dissolved alkali metal cation salt of the cyanoacetate ester anion or malonate diester anion. For illustration, the following equation shows the formation of dimethyl malonate anion sodium salt in solution from dimethyl malonate by reaction with sodium methoxide, which is driven to completion by distilling the resulting methanol from the solvent:

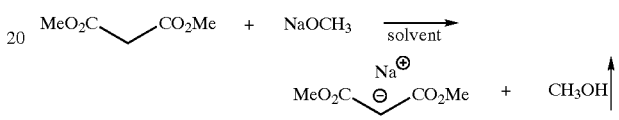

The alkali metal alkoxide may be supplied in solid form or in a solution in the corresponding alcohol, for example, sodium methoxide in methanol. In the latter case, the alcohol supplied as solvent for the alkoxide is also distilled out of the reaction solution to pull the acid-base reaction to completion.

The reaction of the cyanoacetate ester anion or malonate diester anion with the 2-halonitroarene is conducted in a reaction inert solvent system comprising an aprotic polar solvent, as described above. Typically, the same solvent system is used to generate the cyanoacetate ester anion or malonate diester anion in solution from the cyanoacetate ester or malonate diester, respectively, and to subsequently react the cyanoacetate ester anion or—malonate diester anion reaction with the 2-halonitroarene.

The resulting 2-nitroaryl-α-cyanoacetate esters (for example, structural formula (VI)) or 2-nitroarylmalonate diester (for example, structural formula (VII)) are more acidic than the corresponding cyanoacetate esters (for example, structural formula (X)) and malonate diesters (for example, structural formula (XI)), respectively, from which they are produced. Accordingly, when one equivalent of 2-nitroaryl-α-cyanoacetate ester or 2-nitroarylmalonate diester is produced by reaction of one equivalent of 2-halonitroarene with one equivalent of cyanoacetate ester anion or malonate diesters anion, respectively, it then protonates a second equivalent of cyanoacetate ester anion or malonate diesters anion, respectively, and becomes a 2-nitroaryl-α-cyanoacetate ester anion or a 2-nitroarylmalonate diester anion, respectively. This is shown by the stoichiometries of the following reaction equations, illustrating these reactions in general by the reactions of 2-chloronitrobenzene with sodium dimethyl malonate and with sodium methyl cyanoacetate.

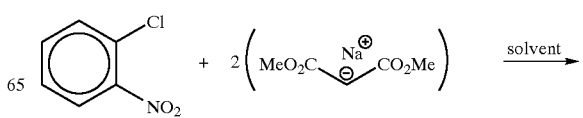

-continued

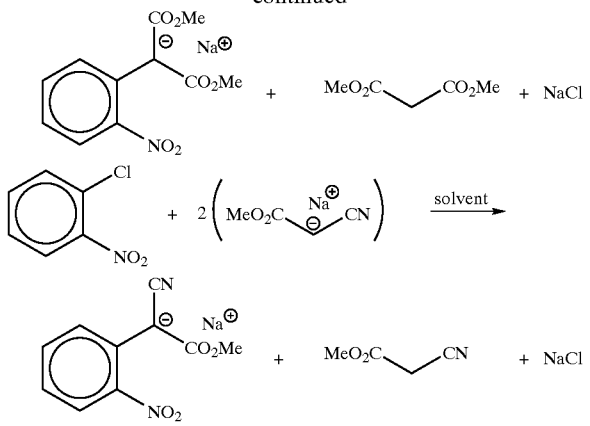

Accordingly, at least 2 equivalents of cyanoacetate esters anion or malonate diester anion is typically used in order to react essentially all the 2-halonitroarene. Typically, an excess of cyanoacetate ester anion or malonate diester anion, greater than the 2 equivalents per 2-halonitroarene, usually 1% to 25% greater, is provided to ensure essentially complete reaction of the 2-halonitroarene in a timely manner.

The reaction is conducted under temperature and time conditions sufficient to essentially complete the conversion of the 2-halonitroarene (or the cyanoacetate ester anion or malonate diester anion, if it is limiting). Such conditions are known in the art and can be readily determined by persons skilled in the art by routine experimentation. Typically, elevated temperatures, usually 50–150° C., is used to conduct and complete the reaction.

The resulting mixture containing the so-produced 2-nitroaryl-α-cyanoacetate ester anion or a 2-nitroarylmalonate diester anion is acidified to protonate the anions and produce the 2-nitroaryl-α-cyanoacetate ester or 2-nitroarylmalonate diester. Any protic acid is suitable for this purpose. Protic acids which are readily separated from the organic products, as the acid itself and as its salt after neutralization, by extraction into water are preferred. Particularly preferred are inexpensive aqueous inorganic acids like hydrochloric, sulfuric, phosphoric and the like. Typically, the reaction mixture containing the 2-nitroaryl-α-cyanoacetate ester anion or a 2-nitroarylmalonate diester anion, after optionally removing some or all of the solvent by distillation or evaporation, is partitioned between an acidic aqueous solution and an organic solution, whereby the anion is protonated and extracts into the organic layer, while the protic acid and its neutralized salt remain in the aqueous solution. The 2-nitroaryl-α-cyanoacetate ester or a 2-nitroarylmalonate diester may be recovered from the separated organic solution in crude or purified form by known methods, or the organic solution may be used directly in the next process reaction.

The alcoholysis of the 2-nitroaryl-α-cyanoacetate ester to produce a 2-nitroarylmalonate diester can be accomplished by methods well known in the art for the alcoholysis of cyano groups to ester groups. Typical methods involve reacting with the alcohol in the presence of an acid. A preferred method is the Pinner synthesis, comprising the addition of dry HCl to a mixture of the cyano compound and an alcohol in the absence of water to form the hydrochloride salt of the imino ester (the adduct of the alcohol to the cyano group), followed by the addition of water to hydrolyze the imino ester to the ester, releasing ammonium chloride.

The reaction of the 2-nitroaryl-α-cyanoacetate ester with the alcohol by the Pinner synthesis may be conducted with the alcohol as the solvent or with an additional solvent that is reaction-inert. By reaction-inert solvent is meant a solvent system which does not react with the reactants or products of the reaction, or react unfavorably with the HCl. The term solvent system is used to indicate that a single solvent or a mixture of two or more solvents can be used. Representative solvents are aromatic hydrocarbons such as benzene, toluene, xylene, nitrobenzene, chlorobenzene, aliphatic hydrocarbons such as pentane, hexane; dialkyl ethers such as diethyl ether, diisopropyl ether; and chlorinated hydrocarbons such as methylene chloride, dichloroethylene, carbon tetrachloride, chloroform. In a preferred embodiment, a reaction inert solvent is used as the extracting solvent for the 2-nitroaryl-α-cyanoacetate ester produced in the preceding step (from the 2-halonitroarene and cyanoacetate ester anion, followed by acidification), and this solution, after drying, is used directly in the Pinner synthesis without isolation of the 2-nitroaryl-α-cyanoacetate ester. Typically, the 2-nitroaryl-α-cyanoacetate ester is reacted with at least an equimolar amount of the alcohol in the reaction inert solvent, preferably an excess of the alcohol, and usually at least two-fold the molar amount of 2-nitroaryl-α-cyanoacetate ester. Methanol is the preferred alcohol for the Pinner synthesis.

Suitable conditions for the Pinner synthesis are known in the art and can be readily determined by persons skilled in the art by routine experimentation. The alcoholysis reaction is conducted under temperature and time conditions sufficient to essentially complete the conversion of the 2-nitroaryl-α-cyanoacetate ester. Such conditions are known in the art and can be readily determined by persons skilled in the art by routine experimentation. The reaction is typically conducted at cold to moderate temperatures, usually −10° C. to 40° C., and preferably not more than 25° C., to minimize a side reaction forming methyl chloride and the amide.

Water, typically in excess, is added to the reaction mixture to complete the formation of the 2-nitroarylmalonate diester. Typically, after optionally removing some or all of the alcohol or the solvent by distillation or evaporation, the 2-nitroarylmalonate diester is separated from the resulting aqueous mixture, optionally by using an organic extraction solvent as the carrier. The solvent in the reaction may also serve as the extraction solvent. 2-nitroarylmalonate diester may be recovered from the separated organic solution in crude or purified form by known methods, or the organic solution may be used directly in the subsequent catalytic hydrogenation reaction.

In the process of the present invention, the steps of catalytically hydrogenating the 2-nitroarylmalonate diester, cyclizing in situ the resulting 2-(N-hydroxyamino)arylmalonate diester and/or 2-aminoarylmalonate diester, and subsequently hydrolyzing and decarboxylating in situ the resulting N-hydroxy-2-oxindole-3-carboxylate ester and/or 2-oxindole-3-carboxylate ester to produce the N-hydroxy-2-oxindole and/or the 2-oxindole, are conducted in the same reaction solution without any separation or isolation of these reaction intermediates between the 2-nitroarylmalonate diester and the N-hydroxy-2-oxindole and/or the 2-oxindole. For the purposes of the present invention, in situ means in the same reaction solution without any intervening separation or isolation of the reaction intermediates. Typically, the sequential in situ steps are conducted in the same reaction zone as the catalytic hydrogenation. However, embodiments where the reaction solution may be moved from place to place during the process, for example, through a tubular flow reactor, are also included. Applicants also contemplate embodiments wherein the hydrogenation catalyst may be separated from the solution prior to the completion of the in situ cyclization, hydrolysis, and decarboxylation steps in the same solution without any separation or isolation of the reaction intermediates.

Suitable temperatures, pressures, solvents, catalysts, and other reaction conditions for the catalytic hydrogenation of nitroarenes are well known in the art and can be readily determined by one skilled in the art. (Reviews: Freifelder, M., *Practical Catalytic Hydrogenation*, Wiley-Interscience, New York, 1971, pp. 168–206; Rylander, P., *Catalytic Hydrogenation in Organic Synthesis*, Academic Press, New York, 1979, pp. 114–137.) Typical conditions suitable for the hydrogenation of nitroarenes in general are suitable for the catalytic hydrogenation of the 2-nitroarylmalonate diester.

The in situ cyclization of the 2-(N-hydroxyamino) arylmalonate diester or 2-aminoarylmalonate diester to the N-hydroxy-2-oxindole-3-carboxylate ester or 2-oxindole-3-carboxylate ester, respectfully, usually occurs readily under typical conditions for catalytic hydrogenation of nitroarenes. If it does not occur under specific conditions chosen for the catalytic hydrogenation, it can be made to occur in a timely manner by raising the temperature of the reaction solution. Usually, temperatures not more than 100° C. are required to essentially complete the in situ cyclization reaction.

The in situ hydrolysis and decarboxylation of the N-hydroxy-2-oxindole-3-carboxylate ester or 2-oxindole-3-carboxylate ester may occur under such typical nitroarene hydrogenation conditions, depending on the specific substrate, the solvent, water content and acidity of the solution, and the precise conditions. When the in situ hydrolysis and decarboxylation reactions are not completed in a timely manner under the conditions chosen for the catalytic hydrogenation, they can be driven to completion in situ by raising the temperature of the reaction solution. Usually, temperatures not more than 150° C. are required to essentially complete the in situ hydrolysis and decarboxylation reactions even when no water or acid is provided in the charged reaction solution.

When the 2-oxindole is the desired product, and the catalytic hydrogenation of the N-hydroxy-2-oxindole is not sufficiently completed in a timely manner under the conditions chosen for the initial catalytic hydrogenation, it can be driven to completion by providing more forcing conditions of higher temperature, higher hydrogen pressure, more catalyst, more active catalyst, efficient gas-liquid mixing, or combinations thereof. Suitable combinations of such conditions can be determined by routine experimentation. Applicants have routinely completed such hydrogenations in a timely manner, with sufficient suitable catalyst, at temperatures not more than 150° C. and hydrogen partial pressures not more than 150 psi.

When the in situ hydrolysis and decarboxylation reactions begin occurring before the desired catalytic hydrogenation steps are completed, the liberated carbon dioxide can dilute or displace hydrogen in the gas phase and thereby retard the completion of the desired catalytic hydrogenation steps in a timely manner. Venting the gas phase and repressuring with hydrogen, or flowing hydrogen through the reactor can be used to remove the built up carbon dioxide and effect more timely completion of the desired catalytic hydrogenation steps.

Some or all of the reaction steps of catalytic hydrogenations, cyclization, and hydrolysis and decarboxylation, may be happening simultaneously in the reaction solution.

Suitable solvents systems for the conversion of the 2-nitroarylmalonate diester to, in all, the 2-oxindoles, N-hydroxy-2-oxindoles, or mixtures thereof are those typically chosen for nitroarene hydrogenation. (See the Freifelder and Rylander references.) The conversion can be conducted in a nonpolar solvent, such as toluene, or a polar solvent, such as alcohols, esters, or carboxylic acids, or mixtures thereof. Examples of suitable ester solvents are methyl acetate and ethyl acetate. Preferred solvents are lower alcohols, for example methanol, ethanol, n-propanol, i-propanol, n-butanol, and t-butanol, and lower carboxylic acids, for example acetic acid and propionic acid. Particularly preferred are ethanol and acetic acid or mixtures thereof.

The solvent for the conversion of the 2-nitroarylmalonate diester to, in all, the 2-oxindoles, N-hydroxy-2-oxindoles, or mixtures thereof may optionally include some added water to still further facilitate the in situ hydrolysis and decarboxylation reactions at a lower temperature or in a more timely manner, or both. The acidity of the solvent may be optionally modified with acids or bases, for example acetic acid or ammonium hydroxide.

Suitable catalysts for the conversion of the 2-nitroarylmalonate diester to, in all, the 2-oxindoles, N-hydroxy-2-oxindoles, or mixtures thereof are homogeneous and heterogeneous catalysts well known in the art for nitroarene hydrogenations. (See the Freifelder and Rylander references.) Typical catalysts are heterogeneous hydrogenation catalysts comprising noble metals, noble metal oxides, or Raney catalysts, optionally applied on a suitable support. Preferred catalysts are palladium, platinum, platinum oxide, and Raney nickel. Particularly preferred catalysts are palladium on carbon and platinum on carbon. The palladium or platinum is usually present at 0.5 to 5.0 percent by weight on the carbon. The ratio of the catalyst to the 2-nitroarylmalonate is not critical, but should be sufficient to complete the hydrogenation steps in a timely manner. The palladium or platinum on carbon catalyst is usually used in an amount of 0.1 to 20 percent by weight, preferably 1 to 10 percent by weight relative to the 2-nitroaryl malonate diester.

The catalyst can be modified by one or more promoters or inhibitors known in the art. (See the Freifelder and Rylander references.). In the conversion of halo-2-nitroaryl malonate diesters to halo-2-oxindoles, it can be desirable to use a catalyst selectively poisoned to inhibit catalytic hydrodehalogenation of the substrate, intermediates, or products. Platinum is usually preferred over palladium in such applications, and suitable inhibitors and conditions are known in the art for hydrogenations of halonitroarenes to haloanilines. For example, platinum on carbon can be inhibited by sulfiding, or by adding hypophosphorous acid or other inhibitors known in the art.

Typically, the hydrogenation steps in the conversion of the 2-nitroarylmalonate diester to, in all, the 2-oxindoles, N-hydroxy-2-oxindoles, or mixtures thereof are conducted under hydrogen pressures from 1 to 20 atmospheres, preferably from 4 to 10 atmospheres. Typically, the temperatures for the overall conversion range from ambient (about 20° C.) to 150° C. Usually, hydrogen pressure is applied at ambient temperature, and heating of the solution begins. The final temperature and pressure are determined as required to produce the desired 2-oxindoles, N-hydroxy-2-oxindoles, or mixtures thereof as discussed above.

After the 2-oxindoles, N-hydroxy-2-oxindoles, or mixtures thereof is produced in the reaction solution, it can be separated, isolated, and recovered according to methods usual to one skilled in the art.

Applicants also contemplate the process of the present invention wherein the catalytic hydrogenation reaction steps comprise catalytic transfer hydrogenation reactions. Catalytic transfer hydrogenation involves the use of molecules other than hydrogen as a source of hydrogen for reduction of organic functional groups, in the present case, aromatic nitro groups. Examples of other such molecules used in the art include secondary alcohols, formic acid and ammonium formates, hydrazine, carbon monoxide plus water, and phosphinic and phosphorous acids and their salts, among others. Both homogeneous and heterogeneous catalysts are used in the art for catalytic transfer hydrogenations of aromatic nitro groups to N-hydroxyamino and amino groups. See Johnstone et al., *Chem. Rev*, vol. 85 (1986), pp. 129–170.

EXAMPLES

Without further elaboration, it is believed that one skilled in the art can, using the preceding description, utilize the present invention to its fullest extent. The following specific examples are, therefore, intended to be merely illustrative, and not limitative of the disclosure in any way whatsoever.

The exemplified catalytic hydrogenation reactions were conducted in stirred tank autoclave reactors having 300 ml internal volume. The autoclaves were equipped with a hollow shaft stirring impeller fitted with a six bladed flat disk turbine. The hollow shaft had a hole high in internal volume for gas inlet and another at the impeller turbine for efficient dispersion of the gas phase through the liquid phase. Each autoclave was fitted with a vertical baffle extending along the internal wall. Resistive electric heating elements were jacketed to each autoclave body and were controlled by a proportioning controller which monitored the liquid solution temperature via a thermocouple. Hydrogen was delivered to each autoclave via feed-forward pressure regulators. The hydrogenation reactions were conducted in fed-batch mode, with a batch of 2-nitroarylmalonate diester solution and catalyst and a continuous regulated feed of hydrogen into the autoclave to maintain the set autoclave pressure. Hydrogen uptake was monitored by the pressure drop upstream from the feed-pressure regulator.

Example 1

Preparation of Dimethyl 4-Chloro-2-nitrophenyl Malonate from 2,5-Dichloronitrobenzene and Dimethyl Malonate A solution of dimethyl malonate (30.25 g, 0.229 mol) and dimethylformamide (80 mL) was heated to 45° C. and treated with 25% sodium methoxide in methanol (50 mL). Methanol was distilled out at 300 mmHg vacuum, removing 54 mL at a final temperature of 95° C. The resulting mixture of sodium dimethyl malonate in dimethylformamide was cooled to 80° C. and a solution of 2,5-dichloronitrobenzene (20.0 g, 0.104 mol) in dimethylformamide (20 mL) was added over 10 minutes. The reaction mixture was heated at 95° C. for 2 hours to complete the reaction, forming sodium dimethyl 4-chloro-2-nitrophenyl malonate. Vacuum distillation at 40 mmHg removed 55 mL of dimethylformamide. The reaction mixture was cooled and partitioned between water (120 mL) and toluene (100 mL). Then 6N HCl (25 mL) was added to protonate the sodium dimethyl 4-chloro-2-nitrophenyl malonate. The layers were separated and the organic layer was washed with water (2×50 mL). Concentration of the organic layer by evaporation under vacuum afforded 38.7 g of an oil (comprising 78% dimethyl 4-chloro-2-nitrophenyl malonate, by $^1$H-NMR), from which crystals of dimethyl 4-chloro-2-nitrophenyl malonate formed upon standing.

This Example shows the preparation of a 2-nitroarylmalonate diester by reacting a 2-halonitroarene with a malonate diester anion and then acidifying. It also shows the preparation of a crude 2-nitroarylmalonate diester suitable for conversion to a 2-oxindole (see Example 2), without isolation as a purified solid.

Example 2

Preparation of 6-Chloro-2-oxindole from Dimethyl 4-Chloro-2-nitrophenyl Malonate Dimethyl 4-chloro-2-nitrophenyl malonate (30 g, 0.104 mol in an oil prepared according to the method of Example 1), 5% Pt/C (0.15 g), acetic acid (83 mL) and water (3 mL) were charged to an autoclave reactor. The sealed vessel was flushed with nitrogen and then hydrogen was charged to 75 psig. The reaction mixture was mixed with the hydrogen by rapid stirring and heated to 65° C. and maintained at that temperature under 75 psig hydrogen until no further hydrogen uptake was observed. The reaction mixture was then heated to 100° C. to effect the hydrolysis and decarboxylation of 3-carbomethoxy oxindole intermediates. The gas phase containing carbon dioxide was vented, hydrogen was reintroduced at 75 psig and heating was continued at 105° C. under 75 psig hydrogen for 3.5 hr to complete the hydrogenolysis of N-hydroxy oxindole to the oxindole. The reaction mixture was cooled to 60° C. and filtered, to remove the catalyst, under nitrogen pressure (30 psig) through a 7μ metal frit into a nitrogen-filled 250 mL flask. 20 mL of water was added to the filtrate and the mixture was cooled (ice bath) 3 hours to crystallize the product. Filtration, washing the crystals with cold toluene, and drying in vacuo afforded 12.35 g of 6-chloro-2-oxindole as a white solid ($^1$H-NMR). Isolated yield: 71% from 2,5-dichloronitrobenzene.

This Example shows the conversion of a 2-nitroarylmalonate diester to a 2-oxindole by the process of the present invention.

Example 3

Preparation of Dimethyl 5-Chloro-2-nitrophenyl Malonate from 2,4-Dichloronitrobenzene and Dimethyl Malonate A solution of dimethyl malonate (30.25 g, 0.229 mol) and dimethylformamide (80 mL) was heated to 40–50° C. and treated with 25% sodium methoxide in methanol (50 mL). Methanol was distilled at 300 mmHg, with the final conditions being 95° C. and 200 mmHg. The resulting mixture of sodium dimethyl malonate in dimethylformamide was placed in a 70° C. oil bath and a solution of 2,4-dichloronitrobenzene (20.0 g, 0.104 mol) in dimethylformamide (20 mL) was added over 30 min. The reaction mixture was slowly heated to 95° C. (2.5 hour hold) to complete the reaction between the 2,4-dichloronitrobenzene and the sodium dimethyl malonate. Dimethylformamide (50 mL) was distilled out at 40 mmHg and then the reaction mixture was partitioned between water (120 mL) and toluene (100 mL). Then 6N HCl (18 mL) was added to protonate the nitroaryl malonate anions. The layers were separated and the organic layer was washed with water (3×, 30 mL). Concentration of the organic layer by evaporation under vacuum afforded 37.3 g of an oil containing a 85:15 mixture of dimethyl 5-chloro-2-nitrophenyl malonate and dimethyl 3-chloro-4-nitrophenyl malonate, in quantitative yield from 2,4-dichloronitrobenzene ($^1$H-NMR).

This Example shows the preparation of a crude 2-nitroarylmalonate diester suitable for conversion to a 2-oxindole without isolation as a purified solid. For 2,4-dichloronitrobenzene, about 15% of the substitution occurs for the chloro para to the nitro to give the dimethyl 3-chloro-4-nitrophenyl malonate. This by-product can be carried into the conversion of the dimethyl 5-chloro-2-nitrophenyl malonate into 5-chloro-2-oxindole (Example 4).

Example 4

Preparation of 5-Chloro-2-oxindole from Dimethyl 5-Chloro-2-nitrophenyl Malonate Crude product mixture from Example 3 (Oil containing 0.101 mol of the mixed dimethyl chloronitrophenyl malonates and 10 mL toluene), 5% Pt/C (0.15 g), ammonium hydroxide (0.1 g), acetic acid (80 mL) and water (2 mL) were charged to an autoclave reactor. The sealed vessel was flushed with nitrogen and then hydrogen was charged to 75 psig. The reaction mixture was mixed with the hydrogen by rapid stirring and heated to 60° C. and maintained at that temperature until no more hydrogen uptake was observed (30 min). Then, it was heated to 105° C. to effect the hydrolysis and decarboxylation of 3-carbomethoxy-2-oxindole intermediates. The gas phase containing carbon dioxide was vented, hydrogen was reintroduced at 75 psig, and the temperature was maintained at 110–114° C. for 5.5 hr under 75 psig hydrogen pressure to complete the catalytic hydrogenation of N-hydroxy-2-oxindole to 2-oxindole. The reaction mixture was then cooled to 70° C. and filtered free of catalyst into a 250 mL nitrogen filled flask. Then 15 mL of warm water was added and the mixture was allowed to cool to room temperature. After cooling in an ice bath for 3 hr, the resulting slurry was filtered and the solid was washed with cold toluene. The solid was dried in vacuo affording 10.35 g of 5-chloro-2-oxindole ($^1$H-NMR). Isolated yield: 61% from 2,4-dichloronitrobenzene. In the process the dimethyl 3-chloro-4-nitrophenyl malonate was hydrogenated to dimethyl 3-chloro-4-aminophenylmalonate, which then survived substantially as such and remained in the filtrate ($^1$H-NMR, HPLC).

The example shows the conversion of a 2-nitroarylmalonate diester to a 2-oxindole by the process of the present invention. It further shows that ester groups of the isomeric dimethyl 3-chloro-4-nitrophenyl malonate, which cannot form a cyclized oxindole structure by intramolecular ester aminolysis, are not readily hydrolyzed and decarboxylated under the exemplified conditions, but survive as ester groups through the process. This highlights, by comparison the surprising facility with which the 3-carboxylate ester groups in the cyclized oxindole structure can be hydrolyzed and decarboxylated.

Example 5

Preparation of Dimethyl 4-Chloro-2-nitrophenyl Malonate from 2,5-Dichloronitrobenzene and Dimethyl Malonate A solution of dimethyl malonate (91 g, 0.69 mol) in dimethylsulfoxide (300 mL) was treated with 25% sodium methoxide in methanol (143.5 mL). Methanol was removed by distillation (20 mmHg, 40° C.). To this solution of sodium dimethyl malonate was added 2,5-dichloronitrobenzene (60 g, 0.31 mol). The reaction mixture was heated at 90° C. for 2 hours to complete the reaction, forming sodium dimethyl 4-chloro-2-nitrophenyl malonate. After cooling, water (400 mL) was added followed by concentrated HCl (100 mL). The dimethyl 4-chloro-2-nitrophenyl malonate product was extracted into 1:1 toluene:hexane (2×200 mL). The combined organic layers were washed with water (3×100 mL) and concentrated by evaporation under vacuum. The crude product was recrystallized from hexane/ethyl acetate (400 mL, 3:1) to afford 70.5 g of dimethyl 4-chloro-2-nitrophenyl malonate as off-white crystals. Isolated yield: 79% on 2,5-dichloronitrobenzene.

This Example shows the preparation of a 2-nitroarylmalonate diester by reacting a 2-halonitroarene with a malonate diester anion and then acidifying, using an alternative solvent system to that exemplified in Example 1.

Example 6

Preparation of 6-Chloro-2-oxindole from Dimethyl 4-Chloro-2-nitrophenyl Malonate Dimethyl 4-chloro-2-nitrophenyl malonate prepared in Example 5 (25 g, 0.087 mol), 5% Pt/C (sulfided) (100 mg), and reagent ethanol (120 mL), were charged to an autoclave reactor. The sealed vessel was flushed with nitrogen and then hydrogen was charged to 150 psig. The reaction mixture was mixed with the hydrogen by rapid stirring and heated (with exothermic reaction) to 50° C. and maintained at that temperature until hydrogen uptake slowed. The reaction mixture was then heated to 100° C. for 60 minutes to effect the hydrolysis and decarboxylation of 3-carbomethoxy oxindole intermediates. The gas phase containing carbon dioxide was vented, hydrogen was reintroduced, and the mixture was heated to 125° C. to complete the hydrogenation of the N-hydroxy-2-oxindole. The reaction mixture was cooled, diluted with ethanol and hot filtered through a celite pad to remove the catalyst. The resulting ethanol solution was concentrated to 120 mL and then heated to redissolve all solids. Cooling (room temperature, 2 hours), filtration, and drying in vacuo afforded 9.1 g of 6-chloro-2-oxindole as off-white needles. Isolated yield: 62% from dimethyl 4-chloro-2-nitrophenyl malonate.

This Example shows the conversion of a 2-nitroarylmalonate diester to a 2-oxindole by the process of the present invention in a nonacidic solvent, ethanol, without any water provided, so that the only water available to the reaction is that generated by reduction of the nitro group. This further highlights the surprising facility with which the 3-carboxylate ester groups in the cyclized oxindole structure are hydrolyzed and decarboxylated, apparently by their own intrinsic reactivity (without benefit of acid catalyst) towards even low concentrations of water.

Example 7

Preparation of Dimethyl 4-Bromo-2-nitrophenyl Malonate from 2,5-Dibromonitrobenzene and Dimethyl Malonate The procedure of Example 5 was applied to 2,5-dibromonitrobenzene (50 g, 0.178 mol). The recrystallization of the crude product afforded 43 g of dimethyl 4-bromo-2-nitrophenyl malonate ($^1$H-NMR). Isolated yield: 73% on 2,5-dibromonitrobenzene.

This Example shows that 2-nitroarylmalonate diesters can be prepared by reacting 2-bromonitroarenes, as well as 2-chloronitroarenes (as in Example 5) by reacting with a malonate diester anion and then acidifying. Quallich et al. disclosed that 2-fluoro-, 2-chloro-, and 2-bromo-nitroarenes were all suitable for conversion to dimethyl 2-nitroarylmalonate by reaction with sodium dimethyl malonate, then acidifying (using $NH_4Cl$).

Example 8

Preparation of 6-Bromo-2-oxindole from Dimethyl 4-Bromo-2-nitrophenyl Malonate The procedure of Example 6 was applied to the dimethyl 4-bromo-2-nitrophenylmalonate prepared in Example 7 (20 g) to afford 12.5 g 6-bromo-2-oxindole ($^1$H-NMR). Isolated yield: 97% on dimethyl 4-bromo-2-nitrophenylmalonate.

This Example shows another conversion of another 2-nitroarylmalonate diester to a 2-oxindole by the process of the present invention in a nonacidic solvent, ethanol, even without any water provided, again highlighting the inventive process with in situ hydrolysis and decarboxylation of 2-oxindole 3-carboxylate ester intermediates.

Example 9

Preparation of Dimethyl 4-Methoxy-2-nitrophenyl Malonate from 5-Methoxy-2-chloronitrobenzene and Dimethyl Malonate To a solution of dimethyl malonate (15.5 g, 0.117 mol) in dimethylsulfoxide (30 mL) was added 25% sodium methoxide in methanol (23 g, 0.102 mol). The methanol was removed by distillation under reduced pressure at 35–40° C. 5-methoxy-2-chloronitrobenzene (10 g, 0.053 mol) was added to the dimethylsulfoxide solution. The resulting mixture was heated for 5.5 hours at 105–115° C. to achieve high conversion of the 5-methoxy-2-chloronitrobenzene. After cooling, water (20 mL) and conc. HCl (30 mL) were added. This mixture was extracted with 1:1 toluene/hexane (2×100 mL). The combined organic extracts were washed with water (30 mL, 2×) and concentrated by evaporation under vacuum to afford 16.4 g of a dark colored solid. While dimethyl 4-methoxy-2-nitrophenylmalonate was the major product, it represented less than 50% of this solid by HPLC area % analysis (254 nm detection).

The Example shows that substituted 2-nitroarylmalonate diesters comprising an electron donating substituent like methoxy can be obtained by reacting so-substituted 2-halonitroarenes with a malonate diester anion and then acidifying, but that the yields of such substituted 2-nitroarylmalonate diesters can be less than desired when prepared by this method. Quallich et al. isolated a 33% yield of the corresponding diethyl ester from a similar reaction of 5-methoxy-2-chloronitrobenzene and sodium diethyl malonate.

Example 10

Preparation of Methyl 4-Methoxy-2-nitrophenyl-α-cyanoacetate from 5-Methoxy-2-chloronitrobenzene and Methyl Cyanoacetate To a solution of methyl cyanoacetate (31 g, 0.313 mol) in dimethylsulfoxide (60 mL) was added 25% sodium methoxide in methanol (62 g, 0.287 mol). The methanol was removed by distillation under reduced pressure at 35–40° C. 5-methoxy-2-chloronitrobenzene (20 g, 0.107 mol) was added to the dimethylsulfoxide solution. This solution was heated for four hours at 100–110° C., to complete the formation of sodium methyl 4-methoxy-2-nitrophenyl-α-cyanoacetate. After cooling, water (100 mL) and conc. HCl (40 mL) were added. This mixture was extracted twice with toluene (100 mL). The combined toluene extracts were washed with water (100 mL, 2×) and concentrated by evaporation under vacuum to afford 32.96 g of a dark colored solid, comprising methyl 4-methoxy-2-nitrophenyl-α-cyanoacetate as the major component (HPLC). A portion of this solid (7.3 g) was dissolved in hot ethanol (50 mL) and treated with water (50 mL). Cooling (0° C.) and filtration afforded 5.0 g of methyl 4-methoxy-2-nitrophenyl-α-cyanoacetate as an off-white solid ($^1$H-NMR). Isolated yield: 85% on 5-methoxy-2-chloronitrobenzene.

This Example demonstrates that a substituted 2-halonitrobenzene comprising an electron-donating substituent like methoxy that does not afford the 2-nitrophenylmalonate diester in good yield on reaction with a malonate diester anion (as in Example 9), will react with a cyanoacetate ester anion to afford the 2-nitroaryl-α-cyanoacetate ester in good yield.

Example 11

Preparation of Dimethyl 4-Methoxy-2-nitrophenyl Malonate from Methyl 4-Methoxy-2-nitrophenyl-α-cyanoacetate A 80 mL Fischer-Porter® bottle (Fischer-Porter Co., Warminster, Pa.) equipped with a gas pressure head and a magnetic stirring bar was charged with methyl 4-methoxy-2-nitrophenyl-α-cyano-acetate from Example 10 (5.0 g, 0.020 mol), methanol (3 mL), toluene (50 mL), sealed, and then charged with HCl gas (55 psig). After stirring for 4 hours at ambient temperature, the apparatus was vented and water (50 mL) was added. The toluene layer was separated and evaporated to dryness under vacuum to afford 5.1 g of dimethyl 4-methoxy-2-nitrophenylmalonate as a tan colored solid ($^1$H-NMR). By HPLC area % analysis (254 nm), the solid was 95% dimethyl 4-methoxy-2-nitrophenylmalonate and 5% methyl 4-methoxy-2-nitrophenyl-α-carbamido-acetate. Isolated yield: 86% on methyl 4-methoxy-2-nitrophenyl-α-cyanoacetate.

This Example shows an alcoholysis of a 2-nitroaryl-α-cyanoacetate ester to produce a 2-nitroarylmalonate diester. This Example, with Example 10, shows that a substituted 2-nitroarylmalonate diester comprising an electron-donating substituent like methoxy, that is not obtained in satisfactory yield by reaction of the corresponding substituted 2-halonitrobenzene with a malonate diester anion (as in Example 9), can obtained in good overall yield by the process of the present invention comprising reacting a 2-halonitroarene with a cyanoacetate ester anion and then acidifying to produce a 2-nitroaryl-α-cyanoacetate ester (as in Example 10); and alcoholyzing the 2-nitroaryl-α-cyanoacetate ester to produce the 2-nitroarylmalonate diester (as in Example 11).

Example 12

Preparation of Dimethyl 4-Methoxy-2-nitrophenylmalonate from 5-Methoxy-2-chloronitrobenzene and Methyl Cyanoacetate To a solution of methyl cyanoacetate (137 g, 1.38 mol) in dimethylsulfoxide (500 mL) was added 280 g of 25% sodium methoxide in methanol (1.30 mol). The methanol was removed by distillation under reduced pressure (100 mmHg) at 40 to 100° C. 5-methoxy-2-chloronitrobenzene (100 g, 0.52 mol) dissolved in dimethylsulfoxide (100 mL) was added to the dimethylsulfoxide solution of sodium methyl cyanoacetate. The resulting mixture was heated at 115° C. for 3 hours. After cooling, (350 mL), water (500 mL), and conc. HCl (125 mL) were added. The toluene layer was separated and the aqueous layer was extracted with toluene (350 mL). The combined toluene extracts were washed with water (3×, 200 mL). Toluene (140 mL) was distilled at ambient pressure to remove traces of water. The remaining toluene solution (containing ca. 118 g methyl 4-methoxy-2-nitrophenyl-α-cyano-acetate, $^1$H-NMR) was used directly in the subsequent alcoholysis step.

Methanol (100 mL, 2.47 mol) was added to the toluene solution. One half of this solution was charged to a 500 mL Fischer-Porter® bottle equipped with a gas pressure head and a magnetic stirring bar. This solution in the sealed bottle was cooled to 0° C. with an ice bath and then HCl (25 psig) was charged. The pressure of HCl was increased to 55 psig over 1 hour as the bath warmed to room temperature. This solution was stirred an additional 3 hours, after which the HCl was vented and water (200 mL) was added to the two phase mixture with stirring. This mixture was stirred for 45 minutes. The toluene layer was separated and the aqueous layer was extracted with toluene (200 mL). The combined organic solutions were concentrated by evaporation under vacuum to afford 75 g of dimethyl 4-methoxy-2-nitrophenylmalonate.

This Example shows the inventive process for preparing a 2-nitroarylmalonate diester, comprising reacting a 2-halonitroarene with a cyanoacetate ester anion and then acidifying to produce a 2-nitroaryl-α-cyanoacetate ester; and alcoholyzing the 2-nitroaryl-α-cyanoacetate ester to produce the 2-nitroarylmalonate diester. This Example further shows the process without isolation of the 2-nitroaryl-α-cyanoacetate ester in purified or solid form.

Example 13

Preparation of 6-Methoxy-2-oxindole from 5-Methoxy-2-chloronitrobenzene and Methyl Cyanoacetate A solution of methyl cyanoacetate (70.1 g, 0.708 mol) in dimethylsulfoxide (200 mL) was treated with 25% sodium methoxide in methanol (153 ml, 0.668 mol). The methanol was removed by distillation at 100 mmHg to a final temperature of 95° C. Then, a solution of 5-methoxy-2-chloronitrobenzene (50.0 g, 0.267 mol) in dimethylsulfoxide (50 mL) was added over 5 minutes. The resulting mixture was heated at 105° C. for 3 hours and then cooled to 40° C. and partitioned between water (250 mL) and toluene (200 mL). Hydrochloric acid (63 mL, 37%) was added and the layers were separated. The toluene layer was extracted with water (3×, 150 mL). This solution was dehydrated by distillation using a Dean-Stark trap and a total of 100 mL toluene/water was distilled off.

Half of this solution of methyl 4-methoxy-2-nitrophenyl-α-cyano-acetate in toluene was charged to a 500 mL Fischer-Porter bottle® and methanol (22 mL) was added. This bottle was sealed, flushed with nitrogen, and chilled with an ice bath. Hydrochloric acid (anhydrous gas, 40 psig) was charged over 30 min. The reaction mixture was stirred at 20° C. for 4 hours. The HCl gas was vented, the bottle was opened and water (100 mL) was added. After stirring for 40 min, the phases were separated and the toluene layer was washed with water (50 mL). The toluene was distilled, removing water (100 ml removed) and replaced with ethanol (2×, 100 mL) by azeotropic distillation (removing 125 ml toluene/ethanol). Additional ethanol (100 mL) was added. By HPLC area % analysis (254 nm) this solution contained 1% methyl 4-methoxy-2-nitrophenyl-α-cyano-acetate, 6.2% methyl 4-methoxy-2-nitrophenyl-α-carboamido-acetate, 8.6% 5-methoxy-2-chloronitrobenzene, and 84% dimethyl 4-methoxy-2-nitrophenylmalonate).

The ethanol solution was transferred to a 300 mL autoclave reactor and acetic acid (2 mL) and 5% Pd/C (0.55 g) were added. The sealed reactor was flushed with nitrogen and charged with hydrogen (80 psig). The reaction mixture was heated to 95° C. and maintained at that temperature under constant 80 psig pressure supplied by hydrogen. When the uptake of hydrogen slowed, the reactor was vented, hydrogen was reapplied and the mixture was heated to 105° C. with occasional venting to remove carbon dioxide and reapplying of hydrogen pressure. After 8 hours at 105° C. and, finally, one hour at 115° C. to further convert remaining N-hydroxy-2-oxindole to the 2-oxindole, the reaction mixture was filtered to remove the catalyst, through an in-line filter under pressure while still hot (55° C.). Cooling in an ice bath for 4 hours and filtration afforded 12.3 g 6-methoxy-2-oxindole as an off-white crystalline solid (Purity 98.0%). Isolated yield: 56% on 5-methoxy-2-chloronitrobenzene.

This Example shows the inventive process for preparing a 2-oxindole, N-hydroxy-2-oxindole, or mixtures thereof comprising: reacting a 2-halonitroarene with a cyanoacetate ester anion and then acidifying to produce a 2-nitroaryl-α-cyanoacetate ester; alcoholyzing the 2-nitroaryl-α-cyanoacetate ester to produce a 2-nitroarylmalonate diester; and converting the 2-nitroarylmalonate diester to the 2-oxindole, N-hydroxy-2-oxindole, or mixtures thereof by the inventive process of catalytic hydrogenation with in situ cyclization and in situ hydrolysis and decarboxylation. It further demonstrates this overall inventive conversion of the 2-halonitroarenes to the 2-oxindoles with no isolations of solid intermediates in purified forms.

Example 14

Preparation of N-Hydroxy-6-chloro-2-oxindole from Dimethyl 4-Chloro-2-nitrophenylmalonate A mixture of dimethyl 4-chloro-2-nitrophenylmalonate (30 g, 0.10 mol), 5% Pt/C (0.15 g), water (3 mL), and acetic acid (95 mL) were charged to an autoclave reactor. The sealed autoclave was flushed with nitrogen, then charged with hydrogen (75 psig). The reaction mixture was mixed with the hydrogen, kept at constant pressure, by rapid stirring. Hydrogen was consumed over 1 hour at 30–40° C. The reaction mixture was then heated to 60° C. for 10 minutes to complete the hydrogenation with in situ cylization forming methyl N-hydroxy-6-chloro-2-oxindole-3-carboxylate. The hydrogen was then vented and replaced with nitrogen. The mixture was then heated at 105° C. for 1 hour to effect the in situ hydrolysis and decarboxylation of N-hydroxy-6-chloro-2-oxindole-3-carboxylate to N-hydroxy-6-chloro-2-oxindole. The reaction mixture was cooled to 80° C. and emptied under nitrogen pressure from the reactor as a slurry. This slurry was stirred under nitrogen until it cooled to 45° C. Filtration afforded a crude product contaminated with the catalyst. This solid was dissolved in hot tetrahydrofuran (450 mL) and filtered through a Celite pad with vacuum. Concentration to 100 mL followed by the addition of hexane (100 mL) afforded a slurry which was filtered. The solid was dried in vacuo to yield 9.85 g of N-hydroxy-6-chloro-2-oxindole ($^1$H-NMR). Isolated yield: 54% on dimethyl 4-chloro-2-nitrophenylmalonate.

This Example shows the inventive process for preparing a N-hydroxy-2-oxindole from a 2-nitrophenylmalonate diester by the process of the present invention.

The present inventions have been shown by both description and examples. The examples are only examples and cannot be construed to limit the scope of the invention. One of ordinary skill in the art will envision equivalents to the inventive processes described by the following claims which are within the scope and spirit of the claimed invention.

I claim as my invention:

1. A process for preparing a 2-oxindole, a N-hydroxy-2-oxindole, or mixtures thereof, comprising:
    A) catalytically hydrogenating a 2-nitroarylmalonate diester to produce a 2-(N-hydroxyamino)arylmalonate diester, a 2-aminoarylmalonate diester, or mixtures thereof as a first reaction intermediate;
    B) cyclizing, by intramolecular aminolysis of one ester group, the first reaction intermediate to produce a N-hydroxy-2-oxindole-3-carboxylate ester, 2-oxindole-3-carboxylate ester, or mixtures thereof as a second reaction intermediate; and
    C) hydrolyzing and decarboxylating the remaining ester group of the second reaction intermediate to produce the N-hydroxy-2-oxindole, the 2-oxindole, or mixtures thereof;
        wherein the cyclization reaction and the hydrolysis and decarboxylation reaction are conducted in situ with the catalytic hydrogenation reaction without isolation of said reaction intermediates.

2. The process of claim 1, further comprising:
    D) catalytically hydrogenating the N-hydroxy-2-oxindole obtained in step C) to produce the 2-oxindole;
        wherein said further catalytic hydrogenation reaction is conducted in situ with the preceding catalytic hydrogenation, cyclization, and hydrolysis and decarboxylation reactions without isolation of the N-hydroxy-2-oxindole.

3. A process of claim 1, wherein the 2-nitroarylmalonate diester starting material is prepared by a process comprising:
    reacting a 2-halonitroarene with a malonate diester anion and then acidifying to produce the 2-nitroarylmalonate diester.

4. The process of claim 3, further comprising:
    D) catalytically hydrogenating the N-hydroxy-2-oxindole obtained in step C) to produce the 2-oxindole;
        wherein said further catalytic hydrogenation reaction is conducted in situ with the preceding catalytic hydrogenation, cyclization, and hydrolysis and decarboxylation reactions without isolation of the N-hydroxy-2-oxindole.

5. A process of claim 1, wherein the 2-nitroarylmalonate diester starting material is prepared by a process comprising:
    reacting a 2-halonitroarene with a cyanoacetate ester anion and then acidifying to produce a 2-nitroaryl-α-cyanoacetate ester; and
    alcoholyzing the 2-nitroaryl-α-cyanoacetate ester to produce the 2-nitroarylmalonate diester.

6. The process of claim 5, further comprising:
    D) catalytically hydrogenating the N-hydroxy-2-oxindole obtained in step C) to produce the 2-oxindole;
        wherein said further catalytic hydrogenation reaction is conducted in situ with the preceding catalytic hydrogenation, cyclization, and hydrolysis and decarboxylation reactions without isolation of the N-hydroxy-2-oxindole.

7. The process of claim 1, 2, 3, 4, 5, or 6 wherein the 2-oxindole is selected from the group consisting of 5-chloro-2-oxindole, 5-bromo-2-oxindole, 6-chloro-2-oxindole, 6-bromo-2-oxindole, and 6-methoxy-2-oxindole.

8. The process of claim 1, 2, 3, 4, 5, or 6 wherein the N-hydroxy-2-oxindole is selected from the group consisting of N-hydroxy-5-chloro-2-oxindole, N-hydroxy-5-bromo-2-oxindole, N-hydroxy-6-chloro-2-oxindole, N-hydroxy-6-bromo-2-oxindole, and N-hydroxy-6-methoxy-2-oxindole.

9. The process of claim 1, 2, 3, 4, 5, or 6 wherein the 2-nitroarylmalonate diester is a dimethyl 2-nitroarylmalonate.

10. The process of claim 1, 2, 3, 4, 5, or 6 wherein the hydrogenation catalyst is selected from the group consisting of palladium and platinum.

11. The process of claim 10 wherein the hydrogenation catalyst is supported on carbon.

12. The process of claim 1, 2, 3, 4, 5, or 6 wherein the process converting the 2-nitroarylmalonate diester to the 2-oxindole, a N-hydroxy-2-oxindole, or mixtures thereof is conducted at a temperature from 20 to 150° C. and at a hydrogen pressure from 1 to 20 atmospheres.

13. The process of claim 1, 2, 3, 4, 5, or 6 wherein the process converting the 2-nitroarylmalonate diester to the 2-oxindole, a N-hydroxy-2-oxindole, or mixtures thereof is conducted in a solvent comprising an alcohol, an ester, a carboxylic acid, or mixtures thereof.

14. The process of claim 13 wherein the solvent comprises ethanol, acetic acid, or mixtures thereof.

15. The process of claim 5 or 6 wherein the alcoholysis reaction comprises an acid catalyzed methanolysis reaction.

16. The process of claim 15 wherein the methanolysis reaction comprises:
    adding dry hydrochloric acid to a mixture of the 2-nitroaryl-α-cyanoacetate ester and methanol to form the corresponding imino ester hydrochloride; and
    adding water to hydrolyze the imino ester hydrochloride to form the dimethyl 2-nitroarylmalonate.

17. The process of claim 5 or 6 wherein the 2-nitroaryl-α-cyanoacetate ester is methyl 2-nitroaryl-α-cyanoacetate.

18. The process of claim 5 or 6 wherein the cyanoacetate ester anion is provided by a process comprising:
    reacting a cyanoacetate ester with an alkali metal alkoxide in a solvent; and
    distilling the corresponding alcohol from the solution to produce a solution of cyanoacetate ester anion alkali metal cation salt in essentially equimolar amount to the provided alkali metal alkoxide.

19. The process of claim 3 or 4 wherein the malonate diester anion is provided by a process comprising:
    reacting a malonate diester with an alkali metal alkoxide in a solvent; and
    distilling the corresponding alcohol from the solution to produce a solution of malonate diester anion alkali metal cation salt in essentially equimolar amount to the provided alkali metal alkoxide.

* * * * *